(12) United States Patent
Takahashi et al.

(10) Patent No.: US 9,975,844 B2
(45) Date of Patent: May 22, 2018

(54) METHOD FOR PRODUCING NITRO COMPOUND

(71) Applicant: SUMITOMO CHEMICAL COMPANY, LIMITED, Tokyo (JP)

(72) Inventors: Teruki Takahashi, Takarazuka (JP); Kazuya Ueki, Takarazuka (JP); Yuta Nagashima, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days. days.

(21) Appl. No.: 15/300,018

(22) PCT Filed: Apr. 8, 2015

(86) PCT No.: PCT/JP2015/061527
§ 371 (c)(1),
(2) Date: Sep. 28, 2016

(87) PCT Pub. No.: WO2015/159905
PCT Pub. Date: Oct. 22, 2015

(65) Prior Publication Data
US 2017/0129846 A1 May 11, 2017

(30) Foreign Application Priority Data

Apr. 17, 2014 (JP) .................................. 2014-085243

(51) Int. Cl.
C07C 201/12 (2006.01)
C07C 209/68 (2006.01)

(52) U.S. Cl.
CPC .......... C07C 201/12 (2013.01); C07C 209/68 (2013.01)

(58) Field of Classification Search
CPC ............................ C07C 201/12; C07C 209/68
See application file for complete search history.

(56) References Cited

U.S. PATENT DOCUMENTS 4,950,756 A 8/1990 Henkelmann et al.
2004/0199002 A1 10/2004 Abe et al.
(Continued)

FOREIGN PATENT DOCUMENTS

JP 2-184657 A 7/1990
JP 2003-171359 A 6/2003
(Continued)

OTHER PUBLICATIONS

International Preliminary Report on Patentability and Written Opinion of the International Searching Authority (Forms PCT/IB/373 and PCT/ISA/237) dated Oct. 18, 2016, for International Application No. PCT/JP2015/061527.
(Continued)

*Primary Examiner* — Jafar Parsa
(74) *Attorney, Agent, or Firm* — Birch, Stewart, Kolasch & Birch, LLP

(57) ABSTRACT

A compound represented by formula (1):

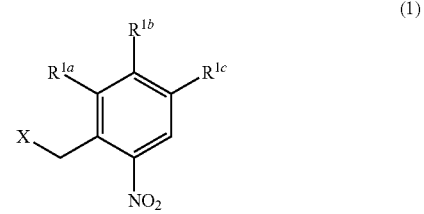

(1)

(wherein, $R^{1a}$ represents an alkyl group having 1 to 6 carbon atoms or the like, $R^{1b}$ and $R^{1c}$ represent a hydrogen atom or the like, and X represents a chlorine atom, a bromine atom or an iodine atom)
can be produced by:
a step wherein a compound represented by formula (2):

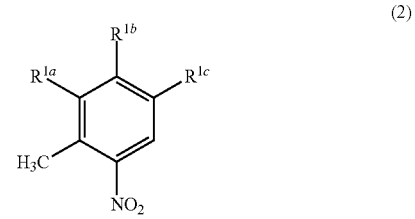

(2)

is reacted with a compound represented by formula (3):

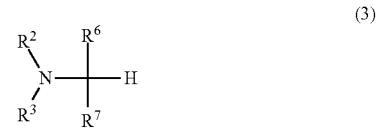

(3)

(wherein, each of $R^2$ and $R^3$ independently represents an alkyl group having 1 to 3 carbon atoms or the like, and each of $R^6$ and $R^7$ independently represents an alkoxy group having 1 to 3 carbon atoms or the like),
thereby obtaining a compound represented by formula (4):

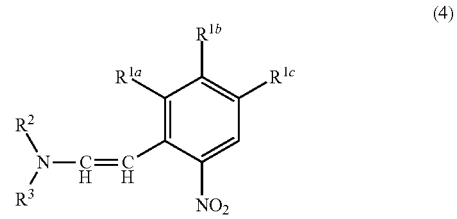

(4)

a step wherein a compound represented by formula (4) is oxidized;
a step wherein the product in the oxidation step is reduced; and a step wherein the product in the reduction reaction is halogenated.

6 Claims, No Drawings

(56) References Cited

U.S. PATENT DOCUMENTS

| | | |
|---|---|---|
| 2010/0130468 A1 | 5/2010 | Boehm et al. |
| 2011/0092485 A1 | 4/2011 | Howbert et al. |
| 2011/0224198 A1 | 9/2011 | Kuduk et al. |

FOREIGN PATENT DOCUMENTS

| | | |
|---|---|---|
| JP | 2010-522238 A | 7/2010 |
| JP | 2012-509343 A | 4/2012 |
| JP | 2013-502430 A | 1/2013 |
| WO | WO 2013/162072 A1 | 10/2013 |

OTHER PUBLICATIONS

Batcho et al., "Indoles from 2-Methylnitrobenzenes by condensation with formamide acetals followed by reduction: 4-Benzyloxyindole", Organic Syntheses, vol. 7, p. 34 (1990), vol. 63, p. 214 (1985).

International Search Report for PCT/JP2015/061527 dated Jul. 14, 2015.

Vetelino et al., "A mild method for conversion of activated aryl methyl groups to carboxaldehydes via the uncatalyzed periodate cleavage of enamines", Tetrahedron Letters, vol. 35, No. 2, pp. 219-222, 1994.

Chinese Office Action and Search Report dated Jul. 3, 2017, for corresponding Chinese Application No. 201580019623.6, including partial English translation.

Siu et al., "Microwave assisted Leimgruber-Batcho reaction for the preparation of indoles, azaindoles and pyrroylquinolines," Org. Biomol. Chem., vol. 2, 2004 (First published as an Advance Article on the web Dec. 16, 2003), pp. 160-167.

METHOD FOR PRODUCING NITRO COMPOUND

TECHNICAL FIELD

The present invention relates to a method for producing a nitro compound.

BACKGROUND ART

WO2013/162072 describes a compound having a control effect on pests and shows that 2-halomethylnitrobenzene such as 2-bromomethyl-3-methylnitrobenzene can be used as a production intermediate thereof.

Further, WO2013/162072 describes that 2-bromomethyl-3-methylnitrobenzene can be produced by reacting 2-hydroxymethyl-3-methylnitrobenzene obtained from 2-methyl-6-nitrobenzoic acid, sodium borohydride and methanesulfonic acid, with boron tribromide. (Reference Production Examples 19 and 20, pages 949 to 951)

SUMMARY OF THE INVENTION

The present invention provides a method for industrially advantageously producing a compound represented by formula (1)

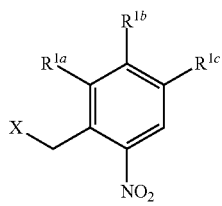

(1)

(wherein X represents a chlorine atom, a bromine atom or an iodine atom, $R^{1a}$ represents an alkyl group having 1 to 6 carbon atoms optionally having a fluorine atom or atoms, or represents a cycloalkyl group having 3 to 6 carbon atoms, $R^{1b}$ and $R^{1c}$ independently represent an alkyl group having 1 to 6 carbon atoms optionally having a fluorine atom or atoms, a hydrogen atom or a cycloalkyl group having 3 to 6 carbon atoms).

According to the present invention, as described below, the compound represented by formula (1) can be industrially advantageously produced by a production method comprising the steps of reacting a compound represented by formula (2) with a compound represented by formula (3) to obtain a compound represented by formula (4), oxidizing the compound represented by formula (4), reducing the product in the oxidation step to obtain a compound represented by formula (8), and halogenating the compound represented by formula (8) to obtain the compound represented by formula (1). Among the compounds represented by formula (4), particularly, a compound represented by formula (4') can also be produced by reacting a compound represented by formula (2) with a compound represented by formula (3) and a secondary amine represented by formula (3').

The present invention is as described below. [1] A method for producing a compound represented by formula (1), comprising the steps of reacting a compound represented by formula (2):

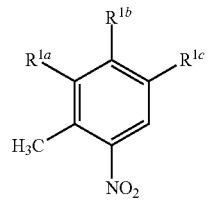

(2)

(wherein $R^{1a}$ represents an alkyl group having 1 to 6 carbon atoms optionally having a fluorine atom or atoms, or represents a cycloalkyl group having 3 to 6 carbon atoms, $R^{1b}$ and $R^{1c}$ independently represent an alkyl group having 1 to 6 carbon atoms optionally having a fluorine atom or atoms, a hydrogen atom or a cycloalkyl group having 3 to 6 carbon atoms), with a compound represented by formula (3):

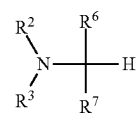

(3)

(wherein $R^2$ and $R^3$ independently represent an alkyl group having 1 to 3 carbon atoms, or $R^2$, $R^3$ and a nitrogen atom bound to $R^2$ and $R^3$ may join together to form a ring, and the ring may contain an oxygen atom as a ring-constituting atom, $R^6$ and $R^7$ independently represent an alkoxy group having 1 to 3 carbon atoms or —$NR^aR^b$, and $R^a$ and $R^b$ independently represent an alkyl group having 1 to 3 carbon atoms, or $R^a$, $R^b$ and a nitrogen atom bound to $R^a$ and $R^b$ may join together to form a ring, and the ring may contain an oxygen atom as a ring-constituting atom), to obtain a compound represented by formula (4):

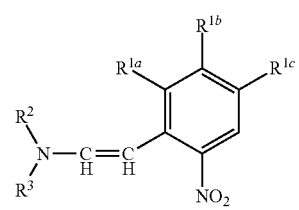

(4)

(wherein $R^{1a}$, $R^{1b}$, $R^{1c}$, $R^2$ and $R^3$ have the same meanings as described above);
oxidizing the compound represented by formula (4) with an oxidizing agent selected from the group consisting of peroxides, permanganates, nitric acid, oxygen and ozone;
reducing a product in the oxidization step to obtain a compound represented by formula (8):

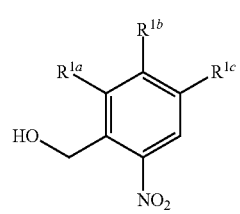

(8)

(wherein $R^{1a}$, $R^{1b}$ and $R^{1c}$ have the same meanings as described above); and halogenating (chlorinating, brominating or iodinating) the compound represented by formula (8) to obtain the compound represented by formula (1):

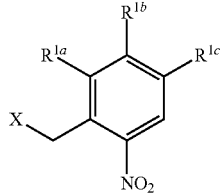
(1)

(wherein X represents a chlorine atom, a bromine atom or an iodine atom, and $R^{1a}$, $R^{1b}$ and $R^{1c}$ have the same meanings as described above).

[2] A method for producing a compound represented by formula (1), comprising the steps of reacting a compound represented by formula (2):

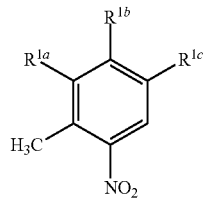
(2)

(wherein $R^{1a}$ represents an alkyl group having 1 to 6 carbon atoms optionally having a fluorine atom or atoms, or represents a cycloalkyl group having 3 to 6 carbon atoms, $R^{1b}$ and $R^{1c}$ independently represent an alkyl group having 1 to 6 carbon atoms optionally having a fluorine atom or atoms, a hydrogen atom or a cycloalkyl group having 3 to 6 carbon atoms), with a compound represented by formula (3):

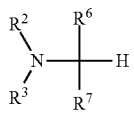
(3)

(wherein $R^2$ and $R^3$ independently represent an alkyl group having 1 to 3 carbon atoms, or $R^2$, $R^3$ and a nitrogen atom bound to $R^2$ and $R^3$ may join together to form a ring, and the ring may contain an oxygen atom as a ring-constituting atom, $R^6$ and $R^7$ independently represent an alkoxy group having 1 to 3 carbon atoms or —$NR^aR^b$, and $R^a$ and $R^b$ independently represent an alkyl group having 1 to 3 carbon atoms, or $R^a$, $R^b$ and a nitrogen atom bound to $R^a$ and $R^b$ may join together to form a ring, and the ring may contain an oxygen atom as a ring-constituting atom), and a secondary amine represented by formula (3'):

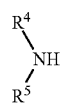
(3')

(wherein $R^4$ and $R^5$ form a ring in which $R^4$, $R^5$ and a nitrogen atom bound to $R^4$ and $R^5$ join together, and the ring may contain an oxygen atom as a ring-constituting atom), to obtain a compound represented by formula (4'):

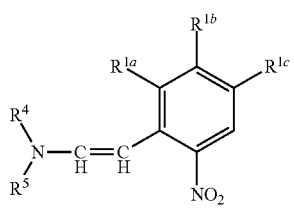
(4')

(wherein $R^{1a}$, $R^{1b}$, $R^{1c}$, $R^4$ and $R^5$ have the same meanings as described above);

oxidizing the compound represented by formula (4') with an oxidizing agent selected from the group consisting of peroxides, permanganates, nitric acid, oxygen and ozone;

reducing a product in the oxidization step to obtain a compound represented by formula (8):

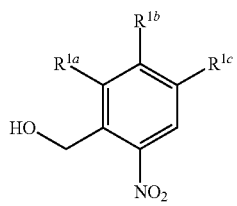
(8)

(wherein symbols have the same meanings as described above); and halogenating (chlorinating, brominating or iodinating) the compound represented by formula (8) to obtain the compound represented by formula (1):

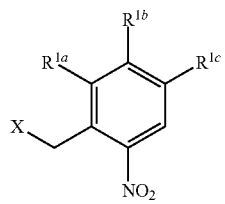
(1)

(wherein X represents a chlorine atom, a bromine atom or an iodine atom, and, $R^{1a}$, $R^{1b}$ and $R^{1c}$ have the same meanings as described above).

[3] The method according to [2], wherein, in the step of reacting a compound represented by formula (2) with a compound represented by formula (3) and a secondary amine represented by formula (3') to obtain a compound represented by formula (4'), the reaction is carried out in the presence of copper iodide.

[4] The method according to any of [1] to [3], wherein, in the step of oxidizing the compound represented by formula (4) or formula (4') with an oxidizing agent, the oxidizing agent is a peroxide, a permanganate or nitric acid.

[5] The method according to any of [1] to [4], wherein, in the step of reducing a product by the oxidation reaction of the compound represented by formula (4) or formula (4') to obtain a compound represented by formula (8), the product is reduced by a borohydride compound.

[6] The method according to any of [1] to [5], wherein, in the step of halogenating the compound represented by formula (8) to obtain the compound represented by formula (1), the compound is halogenated with a phosphorus halide or a phosphorus oxyhalide.

[7] The method according to any of [1] to [6], wherein $R^{1a}$ is a methyl group, and $R^{1b}$ and $R^{1c}$ are a hydrogen atom.

The alkyl group having 1 to 6 carbon atoms optionally having a fluorine atom or atoms in $R^{1a}$, $R^{1b}$ and $R^{1c}$ means an alkyl group having 1 to 6 carbon atoms such as a methyl group, an ethyl group, a propyl group, an isopropyl group, a butyl group, a sec-butyl group, a tert-butyl group, a pentyl group and a hexyl group, and an alkyl group having 1 to 6 carbon atoms in which one or more hydrogen atoms are substituted with a fluorine atom or atoms such as a trifluoromethyl group, a difluoromethyl group, a perfluoroethyl group, a perfluoropropyl group, a perfluoroisopropyl group, a perfluorobutyl group, a perfluoro sec-butyl group, a perfluoro tert-butyl group, a perfluoropentyl group, and a perfluorohexyl group. The alkyl group having 1 to 6 carbon atoms optionally having a fluorine atom or atoms is preferably an alkyl group having 1 to 3 carbon atoms, a trifluoromethyl group, and a difluoromethyl group.

The cycloalkyl group having 3 to 6 carbon atoms in $R^{1a}$, $R^{1b}$ and $R^{1c}$ refers to a cyclopropyl group, a cyclobutyl group, a cyclopentyl group, or a cyclohexyl group. The cycloalkyl group having 3 to 6 carbon atoms is preferably a cycloalkyl group having 3 to 4 carbon atoms.

The alkyl group having 1 to 3 carbon atoms is a methyl group, an ethyl group, a propyl group or an isopropyl group, and the alkyl group having 1 to 3 carbon atoms in $R^2$, $R^3$, $R^a$ and $R^b$ is preferably a methyl group and an ethyl group.

The alkoxy group having 1 to 3 carbon atoms is a methoxy group, an ethoxy group, a propoxy group or an isopropoxy group, and the alkoxy group having 1 to 3 carbon atoms in $R^6$ and $R^7$ is preferably a methoxy group and an ethoxy group.

$R^{1a}$ is preferably an alkyl group having 1 to 3 carbon atoms, and more preferably a methyl group.

$R^{1b}$ and $R^{1c}$ are preferably a hydrogen atom.

In the case where $R^2$, $R^3$ and a nitrogen atom bound to $R^2$ and $R^3$ join together to form a ring, N, $R^2$ and $R^3$ may form a 5- to 7-membered ring containing a nitrogen atom, and the 5- to 7-membered ring may contain an oxygen atom as a ring-constituting atom. Examples of —$NR^2R^3$ having the ring structure described above include a pyrrolidino group, a piperidino group, and a morpholino group.

Preferred —$NR^2R^3$ is a dimethylamino group, a diethylamino group, and a pyrrolidino group.

Examples of —$NR^aR^b$ include a dimethylamino group, a diethylamino group, a morpholino group, a piperidino group, and a pyrrolidino group.

$R^6$ is preferably an alkoxy group having 1 to 3 carbon atoms and —$NR^aR^b$, and a methoxy group and a dimethylamino group are more preferred.

$R^7$ is preferably an alkoxy group having 1 to 3 carbon atoms and —$NR^aR^b$, and a methoxy group and a dimethylamino group are more preferred.

$R^4$, $R^5$ and a nitrogen atom bound to $R^4$ and $R^5$ join together to form a ring, N, $R^4$ and $R^5$ may form a 5- to 7-membered ring containing a nitrogen atom, and the 5- to 7-membered ring may contain an oxygen atom as a ring-constituting atom. Examples of —$NR^4R^5$ having the ring structure described above include a pyrrolidino group, a piperidino group, and a morpholino group.

Preferable —$NR^4R^5$ is a pyrrolidino group.

First, a method for producing a compound represented by formula (4) will be described.

The compound represented by formula (4) is produced by reacting a compound represented by formula (2) with a compound represented by formula (3).

Examples of the compound represented by formula (2) include 2,3-dimethylnitrobenzene, 2-methyl-3-ethylnitrobenzene, 2-methyl-3-cyclopropylnitrobenzene, 2-methyl-3-trifluoromethylnitrobenzene, and 2-methyl-3-difluoromethylnitrobenzene, and a commercially available one may be used, or one prepared by a known method may be used.

Examples of the compound represented by formula (3) include N,N-dimethylformamide dimethyl acetal, N,N-dimethylformamide diethyl acetal, 1-(dimethoxymethyl)pyperidine, 1-(diethoxymethyl)pyperidine, 1-(dimethoxymethyl)pyrrolidine, 1-(diethoxymethyl)pyrrolidine, 4-(dimethoxymethyl)morpholine, 4-(diethoxymethyl)morpholine, bis(N,N-dimethylamino)methoxymethane, dipiperidinomethoxymethane, dipyrrolidinomethoxymethane, dimorpholinomethoxymethane, tri(N,N-dimethylamino)methane, tripiperidinomethane, tripyrrolidinomethane, and trimorpholinomethane, and a commercially available one may be used, or one prepared by a known method may be used. Preferred compound represented by formula (3) is N,N-dimethylformamide dimethyl acetal.

The use amount of the compound represented by formula (3) is at a ratio of usually 1 to 10 mol, and preferably 1 to 3 mol, based on 1 mol of the compound represented by formula (2).

The reaction of the compound represented by formula (2) with the compound represented by formula (3) is usually carried out by mixing both compounds, and a solvent can be used in the mixing.

Examples of the solvent include hydrocarbons such as heptane, hexane, cyclohexane, pentane, toluene and xylene; ethers such as diethyl ether, tetrahydrofuran, 1,4-dioxane, ethylene glycol dimethyl ether, anisole, methyl tert-butyl ether and diisopropyl ether; halogenated hydrocarbons such as carbon tetrachloride, chloroform, dichloromethane, 1,2-dichloroethane, tetrachloroethane and chlorobenzene; nitriles such as acetonitrile and propionitrile; and mixtures thereof, and the solvent is preferably N,N-dimethylformamide.

The use amount of the solvent is usually at a ratio of 0.1 to 50 parts by weight, based on 1 part by weight of the compound represented by formula (2).

The compound represented by formula (2) and the compound represented by formula (3) may be mixed at a time, or may be mixed while gradually adding either compound.

The mixing may be carried out under a nitrogen atmosphere.

The reaction temperature is within the range of usually −20 to 250° C., and preferably 50 to 200° C.

The reaction time is within the range of usually 0.1 to 72 hours, and preferably 1 to 24 hours.

The reaction mixture is concentrated, whereby the compound represented by formula (4) can be isolated. In the isolation, a solvent can be added to extract the compound represented by formula (4), and a base may be added, as necessary.

Examples of the base include sodium hydroxide, potassium hydroxide, sodium carbonate, potassium carbonate, sodium bicarbonate, and ammonia. Examples of the solvent include ethyl acetate, benzene, toluene, xylene, hexane, heptane, chloroform, dichloromethane, diethyl ether, tert-butyl methyl ether, and water. In the case where the base is added in a form of an aqueous solution, the concentration is usually 1 to 6 normal.

The isolated compound represented by formula (4) can be purified by washing, recrystallization, and the like.

Among the compounds represented by formula (4), particularly, a compound represented by formula (4') can be also produced by reacting a compound represented by formula (2) with a compound represented by formula (3) and a secondary amine represented by formula (3').

Specific examples of the compound represented by formula (2) and the compound represented by formula (3) are as described above.

Examples of the secondary amine represented by formula (3') include pyrrolidine, pyperidine, and morpholine.

The use amount of the compound represented by formula (3) is at a ratio of usually 1 to 10 mol, and preferably 1 to 3 mol, based on 1 mol of the compound represented by formula (2), and the use amount of the secondary amine represented by formula (3') is usually at a ratio of 0.05 to 10 mol, based on 1 mol of the compound represented by formula (2).

In the reaction, copper halide may be further added together with the secondary amine. Examples of the copper halide include copper chloride, copper bromide, and copper iodide, and a monovalent copper halide is preferred. The copper halide is usually used in a ratio of 0.001 to 5 mol, based on 1 mol of the compound represented by formula (2).

The reaction of the compound represented by formula (2) with the compound represented by formula (3) and the secondary amine represented by formula (3') is usually carried out by mixing them, and a solvent can be used in the mixing.

Specific examples and the use amount of the solvent are the same as those in the reaction of the compound represented by formula (2) with the compound represented by formula (3).

The mixing may be carried out under a nitrogen atmosphere.

The reaction temperature is within the range of usually −20 to 250° C., and preferably 0 to 150° C.

The reaction time is within the range of usually 0.1 to 72 hours, and preferably 1 to 24 hours.

Post treatment after completion of the reaction is the same as those in the reaction of the compound represented by formula (2) with the compound represented by formula (3).

Examples of the compounds represented by formula (4) and formula (4') include
2-{2-(N,N-dimethylamino)vinyl}-3-methylnitrobenzene,
2-{2-(N,N-diethylamino)vinyl}-3-methylnitrobenzene,
2-(2-pyrrolidinylvinyl)-3-methylnitrobenzene,
2-(2-piperidinylvinyl)-3-methylnitrobenzene,
2-(2-morpholinylvinyl)-3-methylnitrobenzene,
2-{2-(N,N-dimethylamino)vinyl}-3-ethylnitrobenzene,
2-{2-(N,N-diethylamino)vinyl}-3-ethylnitrobenzene,
2-(2-pyrrolidinylvinyl)-3-ethylnitrobenzene,
2-(2-piperidinylvinyl)-3-ethylnitrobenzene,
2-(2-morpholinylvinyl)-3-ethylnitrobenzene,
2-{2-(N,N-dimethylamino)vinyl}-3-cyclopropylnitrobenzene,
2-{2-(N,N-diethylamino)vinyl}-3-cyclopropylnitrobenzene,
2-(2-pyrrolidinylvinyl)-3-cyclopropylnitrobenzene,
2-(2-piperidinylvinyl)-3-cyclopropylnitrobenzene,
2-(2-morpholinylvinyl)-3-cyclopropylnitrobenzene, 2-{2-(N,N-dimethylamino)vinyl}-3-trifluoromethylnitrobenzene,
2-{2-(N,N-diethylamino)vinyl}-3-trifluoromethylnitrobenzene,
2-(2-pyrrolidinylvinyl)-3-trifluoromethylnitrobenzene,
2-(2-piperidinylvinyl)-3-trifluoromethylnitrobenzene, and
2-(2-morpholinylvinyl)-3-trifluoromethylnitrobenzene.

Next, the oxidation reaction of the compound represented by formula (4) will be described. The oxidation reaction of the compound represented by formula (4') can be also carried out in the same manner.

The oxidation reaction is carried out by oxidizing the compound represented by formula (4) with an oxidizing agent selected from the group consisting of peroxides, permanganates, nitric acid, oxygen and ozone.

Examples of the peroxides include peracetic acid, perpropionic acid, m-chloroperbenzoic acid, dimethyldioxirane, tert-butyl hydroperoxide, perbenzoic acid, dibenzoyl peroxide, peroxy-potassium sulfate ($2KHSO_5 \cdot KHSO_4 \cdot K_2SO_4$, Oxone (registered trademark), DuPont Specialty Chemistry, USA), and hydrogen peroxide.

Examples of the permanganate include potassium permanganate, and sodium permanganate.

The preferred oxidizing agents are peroxides, permanganates, and nitric acid.

The oxidizing agent is usually used in a ratio of 0.1 to 50 mol, based on 1 mol of the compound represented by formula (4).

In the oxidation reaction, it is preferred to add an acid, base or salt.

In the case where the oxidizing agent is hydrogen peroxide, it is preferred to add an acid or a base. Specific examples of the acid are acetic acid, formic acid and nitric acid, and specific examples of the base are alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonate, and alkali metal hydroxides such as lithium hydroxide, sodium hydroxide, potassium hydroxide and cesium hydroxide. Also, hydrogen peroxide/sodium tungstate and hydrogen peroxide/titanium-containing catalyst can be used.

In the case where the oxidizing agent is potassium permanganate, it is preferred to add a base. Specific examples of the base include alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonate, and alkali metal hydroxides such as lithium hydroxide, sodium hydroxide, potassium hydroxide and cesium hydroxide.

In the case where the oxidizing agent is nitric acid, it is preferred to add a salt, and specific examples of the salt are alkali metal nitrites such as sodium nitrite and potassium nitrite.

The acid, base or salt described above is usually used in a ratio of 0.01 to 50 mol, based on 1 mol of the compound represented by formula (4).

The oxidation reaction is usually carried out in a solvent. Examples of the solvent include alcohols such as methanol, ethanol, propanol and butanol; hydrocarbons such as heptane, hexane, cyclohexane, pentane, toluene and xylene; ethers such as diethyl ether, tetrahydrofuran, 1,4-dioxane, ethylene glycol dimethyl ether, anisole, methyl tert-butyl ether and diisopropyl ether; halogenated hydrocarbons such as carbon tetrachloride, chloroform, dichloromethane, 1,2-dichloroethane, tetrachloroethane and chlorobenzene; esters such as ethyl acetate and methyl acetate; ketones such as acetone, methyl ethyl ketone and methyl isobutyl ketone; nitriles such as acetonitrile and propionitrile; water, and mixtures thereof.

The use amount of the solvent is usually at a ratio of 0.1 to 50 parts by weight, based on 1 part by weight of the compound represented by formula (4).

The oxidation reaction may be carried out under a nitrogen atmosphere.

The reaction temperature is within the range of usually −20 to 150° C., and preferably 0 to 130° C.

The reaction time is within the range of usually 0.1 to 72 hours, and preferably 1 to 24 hours.

The product obtained by the oxidation reaction is a compound represented by formula (6a):

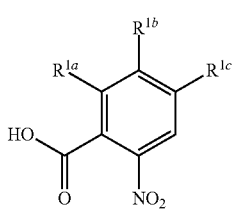
(6a)

(wherein $R^{1a}$, $R^{1b}$ and $R^{1c}$ have the same meanings as described above),
and/or a compound represented by formula (6b):

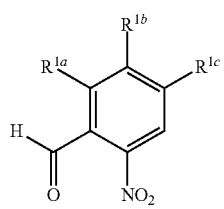
(6b)

(wherein $R^{1a}$, $R^{1b}$ and $R^{1c}$ have the same meanings as described above).

The reaction mixture is concentrated, whereby the compound represented by formula (6a) and/or formula (6b) can be isolated. At this time, an acid, base, salt or solvent may be added to the reaction mixture to isolate the compound, as necessary.

Examples of the acid include hydrogen chloride, and sulfuric acid. Examples of the salt include sodium bisulfate, and ammonium chloride. Examples of the base include sodium hydroxide, potassium hydroxide, sodium carbonate, potassium carbonate, sodium bicarbonate, and ammonia. Examples of the solvent include ethyl acetate, benzene, toluene, xylene, hexane, heptane, chloroform, dichloromethane, diethyl ether, tert-butyl methyl ether, and water. In the case where an acid, base or salt is added in a form of an aqueous solution, the concentration of the acid or base is usually 1 to 6 normal, and the concentration of the salt is usually 1 to 6 mol/L.

The isolated compound can be purified by washing, column chromatography, and the like.

Examples of the compound represented by formula (6a) include 2-methyl-6-nitrobenzoic acid, 2-ethyl-6-nitrobenzoic acid, 2-cyclopropyl-6-nitrobenzoic acid, and 2-trifluoromethyl-6-nitrobenzoic acid.

Examples of the compound represented by formula (6b) include 2-methyl-6-nitrobenzaldehyde, 2-ethyl-6-nitrobenzaldehyde, 2-cyclopropyl-6-nitrobenzaldehyde, and 2-trifluoromethyl-6-nitrobenzaldehyde.

A compound represented by formula (8) can be produced by reducing the product by the oxidation reaction, i.e., the compound represented by formula (6a) and/or formula (6b).

The reduction reaction is usually carried out in a solvent. Examples of the solvent include hydrocarbons such as hexane, cyclohexane, toluene and xylene; ethers such as tetrahydrofuran, 1,4-dioxane, ethylene glycol dimethyl ether, methyl tert-butyl ether and diisopropyl ether; halogenated hydrocarbons such as chloroform, 1,2-dichloroethane and chlorobenzene; acid amides such as N,N-dimethylformamide, 1,3-dimethyl-2-imidazolidinone and N-methylpyrrolidone; sulfoxides such as dimethyl sulfoxide; nitriles such as acetonitrile; alcohols such as methanol, ethanol, propanol and butanol; water; and mixtures thereof.

Examples of the reducing agent include borohydride compounds such as sodium borohydride, borane, borane tetrahydrofuran complex, and borane dimethyl sulfide complex. Further, a borane generated by mixing a borohydride such as sodium borohydride or potassium borohydride with an acid such as sulfuric acid, hydrochloric acid, methanesulfonic acid or boron trifluoride diethyl ether complex or dimethyl sulfate can be used.

The reducing agent is usually used in a ratio of 1 to 10 mol, based on 1 mol of the compound represented by formula (6a) and/or formula (6b) in the reduction reaction.

The reaction temperature is usually within the range of −20 to 100° C.

The reaction time is usually within the range of 0.1 to 72 hours.

After completion of the reaction, the reaction mixture is extracted with an organic solvent, and the organic layer is subjected to post-treatment operations such as drying and concentration, whereby the compound represented by formula (8) can be isolated. The compound represented by formula (8) may also be further purified by operations such as distillation, chromatography, or recrystallization.

The compound represented by formula (1) can be produced by halogenating the compound represented by formula (8). Here, halogenation means chlorination, bromination or iodination. Halogenation is carried out by reacting the compound represented by formula (8) with a halogenating agent (chlorinating agent, brominating agent or iodinating agent).

The reaction is usually carried out in a solvent. Examples of the solvent include hydrocarbons such as hexane, cyclohexane, toluene and xylene; ethers such as tetrahydrofuran, 1,4-dioxane, ethylene glycol dimethyl ether, methyl tert-butyl ether and diisopropyl ether; halogenated hydrocarbons such as chloroform, 1,2-dichloroethane and chlorobenzene; esters such as ethyl acetate and methyl acetate; ketones such as acetone, methyl ethyl ketone and methyl isobutyl ketone; nitriles such as acetonitrile; organic acids such as formic acid, acetic acid and trifluoroacetic acid; water; and mixtures thereof.

Examples of the halogenating agent include bromine, chlorine, sulfuryl chloride, hydrochloric acid, hydrobromic acid, boron tribromide, phosphorus tribromide, trimethylsilyl chloride, trimethylsilyl bromide, thionyl chloride, thionyl bromide, phosphorous oxychloride, phosphorous trichloride, phosphorous pentachloride, thionyl chloride, phosphorous oxybromide, phosphorous pentabromide, phosphorus triiodide, oxalyl dichloride, oxalyl dibromide, acetyl chloride, carbon tetrabromide, N-bromosuccinimide, lithium chloride, sodium iodide, and acetyl bromide. Preferably, the halogenating agent is phosphorus halides such as phosphorous trichloride, phosphorous pentachloride and phosphorus tribromide, and phosphorus oxyhalides such as phosphorous oxychloride.

The amount of the halogenating agent is usually at a ratio of 1 to 10 mol, based on 1 mol of the compound represented by formula (8).

In order to promote the reaction, an additive may be added depending on the halogenating agent to be used, and specifically, the additive can be zinc chloride for acetyl chloride, triphenylphosphine for carbon tetrabromide, dimethyl sulfide for N-bromosuccinimide, boron trifluoride diethyl ether complex for sodium iodide, boron trifluoride diethyl ether complex for acetyl bromide, triethylamine and methanesulfonyl chloride for lithium chloride, aluminum chloride for sodium iodide, trimethylsilyl chloride for sodium iodide, and the like. The use amount of any of the additives is usually at a ratio of 0.01 to 5 mol, based on 1 mol of the compound represented by formula (8).

The reaction temperature is usually within the range of −20 to 150° C.

The reaction time is usually within the range of 0.1 to 24 hours.

After completion of the reaction, the reaction mixture is extracted with an organic solvent, and the organic layer is subjected to post-treatment operations such as drying and concentration, whereby the compound represented by formula (1) can be isolated. The compound represented by formula (1) may be further purified by operations such as distillation, chromatography, or recrystallization.

Examples of the compound represented by formula (1) include 2-chloromethyl-3-methylnitrobenzene, 2-bromomethyl-3-methylnitrobenzene, 2-chloromethyl-3-ethylnitrobenzene, 2-bromomethyl-3-ethylnitrobenzene, 2-chloromethyl-3-cyclopropylnitrobenzene, 2-bromomethyl-3-cyclopropylnitrobenzene, 2-chloromethyl-3-trifluoromethylnitrobenzene, and 2-bromomethyl-3-trifluoromethylnitrobenzene.

EXAMPLES

The present invention will be described in further detail below by way of Examples.

Example 1

A mixture of 30 g of 2,3-dimethylnitrobenzene, 39.5 g of N,N-dimethylforamide dimethylacetal and 200 mL of N,N-dimethylforamide was heated at 175° C. for 10 hours. The reaction mixture was concentrated to obtain 38.0 g of 2-{2-(N,N-dimethylamino)vinyl}-3-methylnitrobenzene

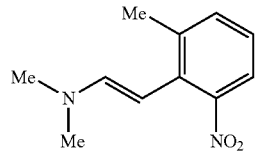 [SMILES: Cc1cccc([N+](=O)[O-])c1/C=C/N(C)C]

$^1$H-NMR (CDCl$_3$) δ (ppm): 2.37 (3H, s), 2.79 (6H, s), 5.01 (1H, d, J=14.0 Hz), 6.29 (1H, d, J=14.0 Hz), 7.01 (1H, t, J=7.8 Hz), 7.27 (1H, d, J=7.2 Hz), 7.37 (1H, d, J=8.2 Hz)

Example 2

A mixture of 10 g of 2,3-dimethylnitrobenzene, 15.8 g of N,N-dimethylforamide dimethylacetal, 27.2 mL of pyrrolidine and 1.26 g of copper (I) iodide was heated at 100° C. for 10 hours. According to $^1$H-NMR measurement of the reaction mixture, it was confirmed that 2-(2-pyrrolidinylvinyl)-3-methylnitrobenzene was obtained in a yield of 97%.

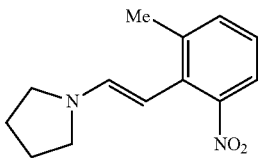 [SMILES: Cc1cccc([N+](=O)[O-])c1/C=C/N1CCCC1]

$^1$H-NMR (CDCl$_3$) δ (ppm): 1.89-1.95 (4H, m), 2.37 (3H, s), 3.20-3.24 (4H, m), 4.95 (1H, d, J=13.8 Hz), 6.62 (1H, d, J=13.8 Hz), 6.96 (1H, t, J=7.8 Hz), 7.25 (1H, d, J=7.5 Hz), 7.36 (1H, d, J=7.9 Hz)

Example 3

A mixture of 10 g of 2,3-dimethylnitrobenzene, 15.8 g of N,N-dimethylforamide dimethylacetal and 27.2 mL of pyrrolidine was heated at 100° C. for 10 hours. According to $^1$H-NMR measurement of the reaction mixture, it was confirmed that 2-(2-pyrrolidinylvinyl)-3-methylnitrobenzene was obtained in a yield of 40%.

Example 4

A mixture of 0.4 g of 2-{2-(N,N-dimethylamino)vinyl}-3-methylnitrobenzene, 1.95 mL of an aqueous hydrogen peroxide solution (30%), 0.97 g of nitric acid (65%) and 10 mL of methanol was stirred at 80° C. for 5 hours. An aqueous sodium bisulfite solution was added to the reaction mixture, and extraction was performed with ethyl acetate. The organic layer was washed with a saturated aqueous sodium bicarbonate solution, dried over anhydrous sodium sulfate, and then concentrated under reduced pressure to obtain 0.28 g of 2-methyl-6-nitrobenzoic acid.

Example 5

A mixture of 4 mg of sodium nitrite and 1.6 g of nitric acid (65%) was heated to 100° C. To this mixture, 0.2 g of 2-{2-(N,N-dimethylamino)vinyl}-3-methylnitrobenzene was added dropwise and stirred at the same temperature for 3 hours. After cooling to room temperature, saturated saline was added to the reaction mixture, and extraction was performed with ethyl acetate to obtain 116 mg of 2-methyl-6-nitrobenzoic acid.

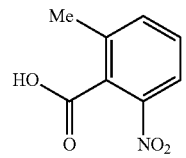

$^1$H-NMR (DMSO-d$_6$) δ (ppm): 2.40 (3H, s), 7.61 (1H, td, J=8.0, 1.7 Hz), 7.74 (1H, d, J=7.6 Hz), 7.99 (1H, d, J=8.2 Hz)

Example 6

A mixture of 5 g of 2-(2-pyrrolidinylvinyl)-3-methylnitrobenzene, 5.10 g of potassium permanganate, 4.46 g of potassium carbonate, 80 mL of acetonitrile and 80 mL of water was stirred at room temperature for 0.5 hours. An aqueous sodium bisulfate solution was added to the reaction mixture, and extraction was performed with ethyl acetate.

The organic layer was washed with a saturated aqueous sodium bicarbonate solution, dried over anhydrous sodium sulfate, and then concentrated under reduced pressure to obtain 2.5 g of 2-methyl-6-nitrobenzaldehyde.

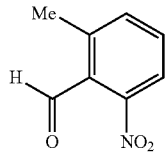

$^1$H-NMR (CDCl$_3$) δ (ppm): 2.48 (3H, s), 7.52 (1H, t, J=7.7 Hz), 7.57 (1H, d, J=7.0 Hz), 7.95 (1H, d, J=8.0 Hz), 10.33 (1H, s)

Example 7

To a mixture of 1.0 g of 2-methyl-6-nitrobenzaldehyde, 10 ml of tetrahydrofuran and 10 ml of methanol, 0.34 g of sodium borohydride was added, and the mixture was stirred at room temperature for 1 hour. A saturated aqueous sodium bicarbonate solution was added to the reaction mixture, and extraction was performed with ethyl acetate. The organic layer was washed with a saturated aqueous sodium bicarbonate solution, dried over anhydrous sodium sulfate, and then concentrated under reduced pressure to obtain 0.96 g of 2-(hydroxymethyl)-3-methyl-1-nitrobenzene.

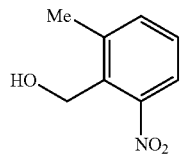

$^1$H-NMR (CDCl$_3$) δ: 2.56 (3H, s), 4.70 (2H, s), 7.35 (1H, t, J=7.9 Hz), 7.48 (1H, d, J=7.6 Hz), 7.71 (1H, d, J=8.2 Hz)

Example 8

A mixture of 22.8 g of sodium borohydride and 240 mL of tetrahydrofuran was stirred at room temperature for 10 minutes. To the mixture, 120 mL of a tetrahydrofuran solution of 75.0 g of 2-methyl-6-nitrobenzoic acid was slowly added dropwise, and after completing the addition, the mixture was further stirred at room temperature for 30 minutes. The reaction mixture was ice-cooled, and 26.9 mL of methanesulfonic acid was added thereto over 2 hours. The mixture was stirred at room temperature for 2 days, then water was added thereto, and extraction was performed with ethyl acetate. The organic layer was sequentially washed with a 10% aqueous hydrochloric acid solution and saturated saline, dried over anhydrous magnesium sulfate, and then concentrated under reduced pressure to obtain 58.9 g of 2-(hydroxymethyl)-3-methylnitrobenzene.

Example 9

A mixture of 100.0 g of 2-methyl-6-nitrobenzoic acid and 1 L of tetrahydrofuran was ice-cooled, and 42.0 g of sodium borohydride was added thereto, followed by adding 139.3 g of dimethyl sulfate, then the mixture was heated to room temperature and stirred for 18 hours. Water was added to the reaction mixture, and extraction was performed with ethyl acetate. The organic layer was sequentially washed with a saturated aqueous sodium bicarbonate solution and saturated saline, dried over anhydrous sodium sulfate, and then concentrated under reduced pressure to obtain 90.9 g of 2-(hydroxymethyl)-3-methylnitrobenzene.

Example 10

A mixture of 58.9 g of 2-(hydroxymethyl)-3-methylnitrobenzene and 620 mL of chloroform was ice-cooled, and 191.0 g of phosphorus tribromide was added dropwise thereto, and then the mixture was stirred at room temperature for 15 hours. Water was added to the reaction mixture, and extraction was performed with ethyl acetate. The organic layer was sequentially washed with water and saturated saline, dried over anhydrous magnesium sulfate, and then concentrated under reduced pressure to obtain 76.7 g of 2-(bromomethyl)-3-methylnitrobenzene.

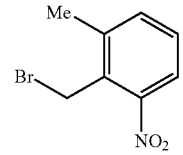 [SMILES: Cc1cccc([N+](=O)[O-])c1CBr]

$^1$H-NMR (CDCl$_3$) δ (ppm): 7.75 (1H, d, J=8.2 Hz), 7.46 (1H, d, J=7.5 Hz), 7.36 (1H, dd, J=8.2, 7.5 Hz), 4.72 (2H, s), 2.54 (3H, s)

INDUSTRIAL APPLICABILITY

According to the present invention, a compound represented by formula (1) used as a production intermediate of a compound having a control effect on pests can be produced.

The invention claimed is:

1. A method for producing a compound of formula (1), comprising the steps of reacting a compound of formula (2):

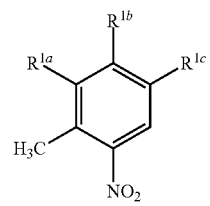

wherein $R^{1a}$ represents an alkyl group having 1 to 6 carbon atoms optionally having a fluorine atom or atoms, or represents a cycloalkyl group having 3 to 6 carbon atoms, $R^{1b}$ and $R^{1c}$ independently represent an alkyl group having 1 to 6 carbon atoms optionally having a fluorine atom or atoms, a hydrogen atom or a cycloalkyl group having 3 to 6 carbon atoms, with a compound of formula (3):

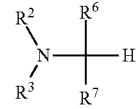

wherein $R^2$ and $R^3$ independently represent an alkyl group having 1 to 3 carbon atoms, or $R^2$, $R^3$ and a nitrogen atom bound to $R^2$ and $R^3$ may join together to form a ring, and the ring may contain an oxygen atom as a ring-constituting atom, $R^6$ and $R^7$ independently represent an alkoxy group having 1 to 3 carbon atoms or —$NR^aR^b$, and $R^a$ and $R^b$ independently represent an alkyl group having 1 to 3 carbon atoms, or $R^a$, $R^b$ and a nitrogen atom bound to $R^a$ and $R^b$ may join together to form a ring, and the ring may contain an oxygen atom as a ring-constituting atom, and a secondary amine of formula (3'):

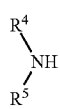
(3')

wherein $R^4$ and $R^5$, $R^4$, $R^5$ and a nitrogen atom bound to $R^4$ and $R^5$ may join together to form a ring, and the ring may contain an oxygen atom as a ring-constituting atom, in the presence of copper iodide to obtain a compound of formula (4'):

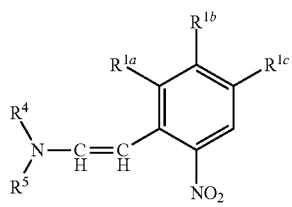
(4')

wherein $R^{1a}$, $R^{1b}$, $R^{1c}$, $R^4$ and $R^5$ have the same meanings as described above;

oxidizing the compound of formula (4') with an oxidizing agent selected from the group consisting of peroxides, permanganates, nitric acid, oxygen and ozone;

reducing a product in the oxidization step to obtain a compound of formula (8):

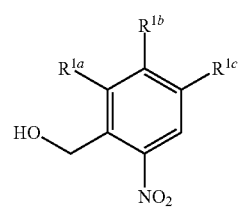
(8)

wherein symbols have the same meanings as described above; and chlorinating, brominating or iodinating the compound of formula (8) to obtain the compound of formula (1):

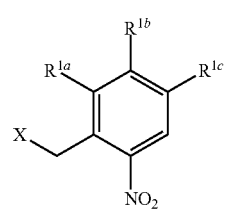
(1)

wherein X represents a chlorine atom, a bromine atom or an iodine atom, and $R^{1a}$, $R^{1b}$ and $R^{1c}$ have the same meanings as described above.

2. The method according to claim 1, wherein the secondary amine is pyrrolidine.

3. The method according to claim 1, wherein, in the step of oxidizing the compound of formula (4') with an oxidizing agent, the oxidizing agent is a peroxide, a permanganate or nitric acid.

4. The method according to claim 3, wherein, in the step of reducing a product by the oxidation reaction of the compound of formula (4') to obtain a compound of formula (8), the product is reduced by a borohydride compound.

5. The method according to claim 1, wherein, in the step of halogenating the compound of formula (8) to obtain the compound of formula (1), the compound of formula (8) is halogenated with a phosphorus halide or a phosphorus oxyhalide.

6. The method according to claim 1, wherein $R^{1a}$ is a methyl group, and $R^{1b}$ and $R^{1c}$ are a hydrogen atom.

* * * * *